United States Patent [19]

Hammann et al.

[11] Patent Number: 5,292,898

[45] Date of Patent: Mar. 8, 1994

[54] PROCESS FOR THE STEREOSELECTIVE PREPARATION OF 5-SUBSTITUTED DELTA-LACTONES AND USE THEREOF

[75] Inventors: Peter Hammann, Babenhausen; Susanne Grabley, Königstein/Taunus; Ernold Granzer, Kelkheim/Taunus; Yvonne Romeyke, Gross-Gerau, all of Fed. Rep. of Germany

[73] Assignee: Hoechst Aktiengesellschaft, Frankfurt am Main, Fed. Rep. of Germany

[21] Appl. No.: 937,718

[22] Filed: Sep. 1, 1992

Related U.S. Application Data

[63] Continuation of Ser. No. 737,715, Jul. 30, 1991, abandoned.

[30] Foreign Application Priority Data

Aug. 1, 1990 [DE] Fed. Rep. of Germany ....... 4024425
Jun. 1, 1991 [DE] Fed. Rep. of Germany ....... 4118009

[51] Int. Cl.$^5$ ............................................. C07D 309/10
[52] U.S. Cl. .................................................... 549/292
[58] Field of Search ........................................ 549/292

[56] References Cited

U.S. PATENT DOCUMENTS

| | | | |
|---|---|---|---|
| 4,970,313 | 11/1990 | Wess et al. | 544/335 |
| 4,977,279 | 12/1990 | Wess et al. | 549/274 |
| 5,091,386 | 2/1992 | Kesseler et al. | 514/277 |

FOREIGN PATENT DOCUMENTS

| | | | |
|---|---|---|---|
| 2010806 | 8/1990 | Canada | C07C 33/02 |
| 0319847 | 6/1989 | European Pat. Off. | C07D 213/55 |
| 0354418 | 2/1990 | European Pat. Off. | C07D 405/06 |
| 0361273 | 4/1990 | European Pat. Off. | C07C 59/42 |

OTHER PUBLICATIONS

Evans et al., *Tetrahedron Lett.*, 27(49), pp. 5939-5942 (1986).
Evans et al., *J. Am. Chem. Soc.*, 108, pp. 2476-2478 (1986).
Tomioka et al., *Tetrahedron Lett.*, 22(17), pp. 1605-1608 (1981).
Lynch et al., *Tetrahedron Lett.*, 28(13), pp. 1385-1388 (1987).
Narasaka et al., *Tetrahedron*, 40(12), pp. 2233-2238 (1984).
Bennet et al., *Heterocycles*, vol. 29, No. 4, pp. 639-642 (1989).
Mizutani et al., *J. Antibiotics*, vol. XLII, No. 6, pp. 952-959 (1989).
Chemical Abstracts, vol. 108, Abstract No. 108:5821b (1988).
Chemical Abstracts, vol. 110, Abstract No. 110:134949q (1989).
Chemical Abstracts, vol. 112, Abstract No. 112:55370g (1990).

*Primary Examiner*—C. Warren Ivy
*Assistant Examiner*—Ba K. Trinh
*Attorney, Agent, or Firm*—Finnegan, Henderson, Farabow, Garrett & Dunner

[57] ABSTRACT

A process for the stereoselective preparation of 5-substituted δ-lactones of the formulae Ia, Ib, Ic and Id

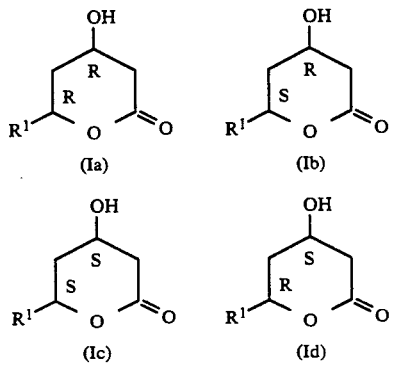

in which $R^1$ is a straight-chain or branched alkyl or alkenyl group or methylhydroxy, novel 5-substituted δ-lactones and novel intermediates, and use thereof as pharmaceuticals having cholesterol synthesis-inhibiting action, fragrances and flavorings is described.

7 Claims, No Drawings

PROCESS FOR THE STEREOSELECTIVE PREPARATION OF 5-SUBSTITUTED DELTA-LACTONES AND USE THEREOF

This is a continuation of application Ser. No. 07/737,715, filed Jul. 30, 1991 now abandoned.

DESCRIPTION

The invention relates to a process for the stereo-selective preparation of 5-substituted δ-lactones, novel 5-substituted δ-lactones and novel intermediates, and use thereof, in particular as pharmaceuticals having cholesterol synthesis-inhibiting action, fragrances and flavorings.

A 5-substituted 3R,5R δ-lactone of the formula Ia

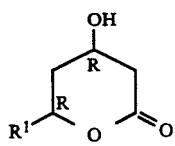

in which $R^1$ is pentyl, has already been prepared enantio-selectively (Bennet and Knight, Heterocycles 29, (1989), 639). The starting compound was methyl-3-oxo-5-hexenal, which was asymmetrically reduced with the aid of yeasts The yield was 22% in an enantiomer purity of 76%.

The object of the present invention is to develop a process with which all stereoisomers of the δ-lactone of the formula Ia can be prepared in high enantiomer purity. A streptenol of the formula

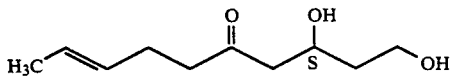

was selected as the starting material. This compound has already been described (Keller-Schierlein, Helvetica Chimica Acta, 66, (1983), 1253) and can be prepared, for example, by Streptomycetes by means of a microbiological process (EP-A 90 103 411.6; Mitzutani, J. Antibiotics, XLII (1989), 952).

The invention therefore relates to a process for the preparation of 5-substituted 3R, 5R, 3R, 5S, 3S, 5S and 3S, 5R δ-lactones of the formula Ia, Ib, Ic or Id

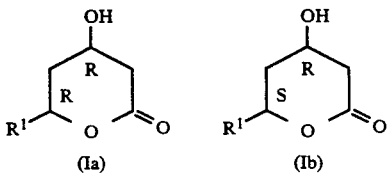

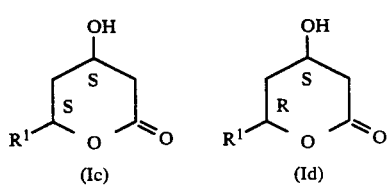

in which $R^1$ is
1) straight-chain or branched alkyl having 3 to 15 carbon atoms,
2) straight-chain or branched alkenyl having 3 to 15 carbon atoms and 1 to 7 C—C double bonds or
3) $CH_2OH$, which comprises
   a) disastereoselectively reducing a compound of the formula IIa

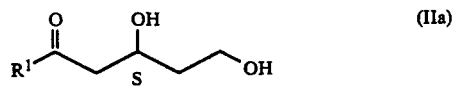

2) to a compound of the formula IIIa or IIIb

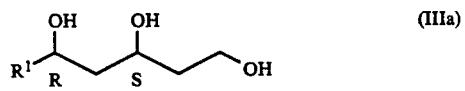

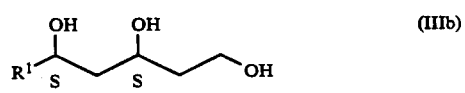

2) regioselectively oxidizing to a compound of the formula Ia or Ib

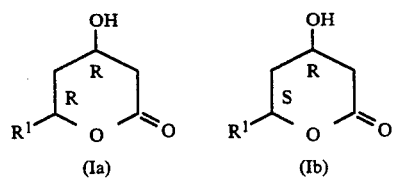

and, if desired,
3) hydrogenating the double bonds of the alkylene chain, or
b) acetalating the compound of the formula IIa to give
   1) a compound of the formula IVa or IVb

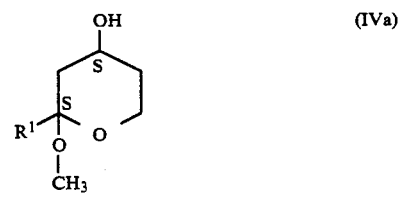

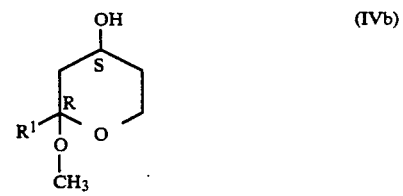

2) oxidizing to give a compound of the formula V

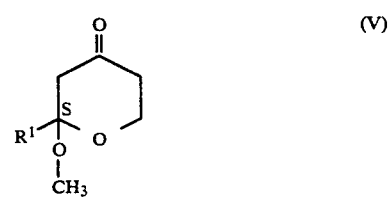

3) disastereoselectively reducing to a compound of the formula IVc

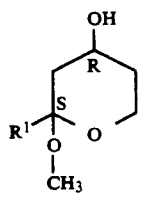 (IVc)

4) deacetalating to give a compound of the formula IIb

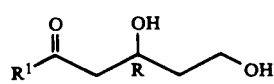 (IIb)

5) disastereoselectively reducing to a compound of the formula IIIc or IIId

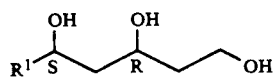 (IIIc)

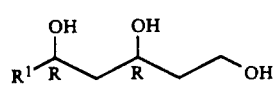 (IIId)

6) regioselectively oxidizing to a compound of the formula Ic or Id

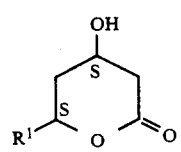 (Ic)

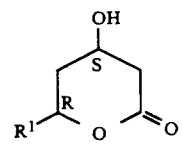 (Id)

and, if desired,
7) hydrogenating the double bonds in the alkylene chain or c) reacting the compound of the formula Ia, Ib, Ic or Id, in which $R^1$ is
   1) straight-chain or branched alkyl having 3 to 15 carbon atoms,
   2) straight-chain or branched alkenyl having 3 to 15 carbon atoms and 1 to 7 C—C double bonds,
   1) with a compound of the formula $R^3$—O to give a compound of the formula

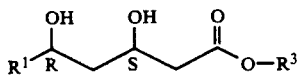 (Va)

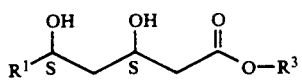 (Vb)

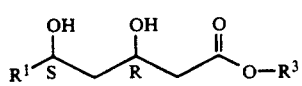 (Vc)

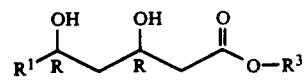 (Vd)

in which $R^3$ is alkyl having 1 to 5 carbon atoms or tertiary butyl, 2) ketalizing with acetone or dimethoxypropane to give a compound of the formula VIa, VIb, VIc or VId

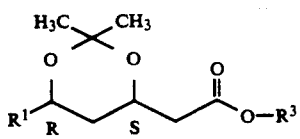 (VIa)

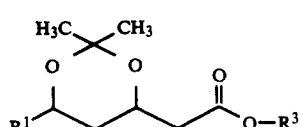 (VIb)

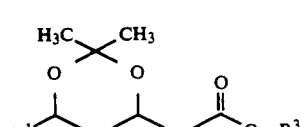 (VIc)

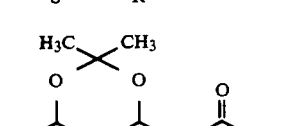 (VId)

3) oxidizing with ozone to give a compound of the formula VIIa, VIIb, VIIc or VIId

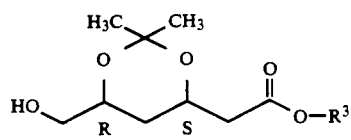 (VIIa)

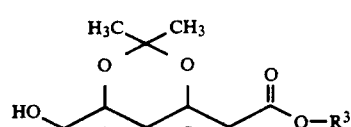 (VIIb)

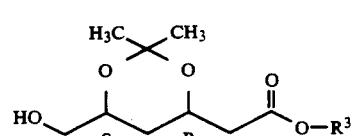 (VIIc)

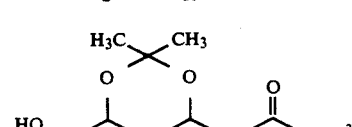 (VIId)

and
4) reacting to give a compound of the formula Ia, Ib, Ic or Id, in which $R^1$ is $CH_2OH$.

The designations R and S signify the absolute configuration at the carbon atom. R is rectus and S is sinister.

All said alkyl and alkylene radicals having more than 3 carbon atoms can be either straight-chain or branched.

The invention also relates to the compounds of the formula Ia, Ib, Ic or Id, excepting the compound Ia in which $R^1$ is a straight-chain alkenyl chain having 5 carbon atoms.

The invention further relates to the compounds of the formula IIb, IIIa, IIIc or IIId, which are suitable as intermediates.

The invention furthermore relates to a process for the preparation of the compounds IIb, IIIa, IIIb, IIIc or IIId.

The compounds of the formula VIIa, VIIb, VIIc or VIId are suitable as precursors for the preparation of cholesterol biosynthesis inhibitors (U.S. Pat. No. 4,970,313).

Those compounds of the formula Ia to Id are preferred in which R is alkyl and alkenyl having 3 to 10 carbon atoms and the alkylene chain has 1 to 5 C—C double bonds Among these compounds, in turn, those of the formula Ia to Id are particularly to be emphasized in which R is alkyl and alkenyl having 5 carbon atoms and the alkylene chain contains 1 or 2 C—C double bonds The compounds of the formula IIa necessary for the preparation of compounds of the formula Ia to Id can be prepared, for example, by the process proposed in European Patent Application No. 90 103 411.6, to which reference is expressly made here. In this case, the compound of the formula IIa is produced by Streptomyces spec., preferably DSM 4356, in a nutrient solution which contains a source of carbon and a source of nitrogen, and customary inorganic salts. Instead of Streptomyces spec. DSM 4356, its mutants and variants can also be employed, if they synthesize these compounds.

The formation of the compound of the formula IIa proceeds particularly well in a nutrient solution which contains soya flour and mannitol in concentrations of in each case 0.5 to 6%, preferably 1 to 4%, relative to the weight of the total nutrient solution.

The fermentation is carried out aerobically, i.e., for example, submerse with shaking or stirring in shaker flasks or fermenters, if desired with the introduction of air or oxygen. The fermentation can be carried out in a temperature range from about 18° to 35° C., preferably at about 25° to 30° C., in particular at 28° to 30° C. The microorganism is cultured under said conditions until the stationary phase is reached, for example for 60 to 120 hours, preferably for 70 to 75 hours.

Advantageously, culturing is carried out in several steps, i.e. one or more precultures are first prepared in a liquid nutrient medium and are then inoculated into the actual production medium, the main culture, for example in the volume ratio 1:10. The preculture is obtained, for example, by inoculating a sporulated mycelium into a nutrient solution and allowing it to grow for about 48 to 72 hours. The sporulated mycelium can be obtained by allowing the strain to grow for about 7 days on a solid or liquid nutrient medium, for example yeast/malt agar.

The compounds of the formula IIa (streptenols) are isolated from the culture medium by known methods taking into account the chemical, physical and biological properties of the products. The compounds of the formula IIa are present in the mycelium or in the culture broth. They can be extracted from the unfiltered culture broth using a water-immiscible or only slightly miscible organic solvent, such as chloroform or ethyl acetate. However, since they are only found to a small extent in the mycelium, it is advantageous to separate the culture broth from the mycelium, for example by centrifugation or filtration, preferably with the addition of filter aids. The compound of the formula IIa can then be isolated from the supernatant or filtrate, expediently in the slightly acidic to neutral pH range, preferably at pH 6 to 7. For this purpose, organic solvents which are only slightly miscible or are immiscible with water can be used, in particular chlorinated hydrocarbons, such as chloroform or methylene chloride, or esters such as ethyl acetate, or acetone.

Instead of extraction, the streptenols can also be isolated from the culture broth by adsorption on commercial adsorber resins. It has also proved advantageous to dry said fermenter contents, for example by spray drying or freeze drying.

The customary process steps, such as chromatography or gel filtration, can be used to isolate the pure streptenols. Chromatography on silica gel has proved particularly suitable, a mixture of ethyl acetate and hexane in a volume ratio of, for example, 1:2 being used an eluent.

In the following, the processes a), b) and c), which enable the 5-substituted δ-lactones of the formulae Ia, Ib, Ic and Id to be stereoselectively prepared, are described in great detail.

In process step a1, a procedure is best used in which the β-hydroxyketone group of the compound IIa is complexed with Lewis acid and reduced with alkoxydialkylborane, if desired in an inert solvent such as diethyl ether or tetrahydrofuran (THF) and then disastereoselectively reduced with NaBH to give a compound of the formula IIIa.

In the preparation of the compound of the formula IIIb, a procedure is best used in which the compound IIa is stereoselectively reduced using $NaHB(OAc)_3$ or $NH_4HB(OAc)_3$ in a suitable solvent, such as acetonitrile, ether, or in mixtures of acetonitrile with glacial acetic acid or ether with glacial acetic acid, to give a compound of the formula IIIb.

The reaction temperatures in this case are between −70° C. and +40° C., in particular between −70° C. and −20 C. The reaction times are 1 to 10 hours, preferably 2 to 4 hours. Completion of the reaction can be determined, for example, by means of thin layer chromatography.

The reductants necessary for the process step, if not commercially available, can prepared in a simple manner by processes known from the literature. Thus, for example, diethylmethoxyborane can be prepared from triethylborane and methanol or $NaHB(OAc)_3$ can be prepared from NaBH. and glacial acetic acid.

In process step a2, a procedure is best used in which the compounds IIIa or IIIb from process step a1 are regioselectively oxidized to the δ-lactone of the formula Ia or Ib using a ruthenium complex (Murahashi, Tetrahedron Lett., 22, (1981), 1605), in particular using $(PPh_3)_3RuCl_2$, in an organic solvent such as $CHCl_3$, $CH_2Cl_2$, acetone or benzene or oxidized by known methods on a platinum or palladium catalyst in the presence of oxygen. The reaction can be carried out using equimolar amounts or, if desired, in the presence of an oxidant, such as, for example, N-methylmorpholine-N-oxide and also with catalytic amounts of the ruthenium complex.

The reaction temperatures in this case are between −70° C. and +70° C., when using a solvent preferably between the solidification point and the boiling point of the solvent, in particular between −20° C. and +30° C. The reaction times are 5 to 60 hours, preferably 20 to 40 hours. Completion of the reaction can be determined, for example, using thin layer chromatography.

In process step a3, a procedure is best used in which the compounds Ia or Ib having a straight-chain or branched alkenyl radical are reacted with hydrogen to give the corresponding compounds of the formula Ia or Ib having a straight-chain or branched alkyl radical by processes known from the literature in the presence of a commercial hydrogenation catalyst in an inert solvent such as methanol, ethanol, isopropanol or ethyl acetate or a mixture of these solvents or an aqueous mixture of these solvents. Commercial hydrogenation catalysts are, for example elements of the 8th group such as platinum, palladium or alternatively nickel, which are usually applied, for example, to active carbon, silica or alumina supports for the purpose of increasing the reactive surface area.

Depending on the catalyst used, the reaction can be carried out either without or with excess hydrogen pressure, for example up to 1 atmosphere. The reaction temperatures are between 0° C. and 40° C., preferably at room temperature. The reaction times are dependent on the batch size and the concentration of the compound to be reduced.

In process step b1, a procedure is best used in which the compound IIa is reacted to give a compound of the formula IVa and IVb in equimolar amounts or in an excess of up to 50-fold of an alcohol such as, for example, methanol, ethanol or isopropanol in the presence of catalytic amounts of a Lewis acid. The reaction can also be carried out, if desired, in an inert solvent such as chloroform, methylene chloride, THF, ethyl acetate or dioxane. Suitable Lewis acids are, for example, copper, iron or lithium halides, in particular $CuCl_2$, $FeCl_3$ or LiBr.

The concentration of the Lewis acid, relative to the compound of the formula IIa, is 0.1 to 5% by weight, preferably 0.1 to 1% by weight. The reaction temperatures are in this case between −40° C. and +100° C., in particular between 0° C. and 30° C., when using a solvent preferably between the solidification point and the boiling point of the solvent, in particular between 0° C. and 30° C. The reaction times are 1 to 180 minutes, preferably 5 to 60 minutes. Completion of the reaction can be determined, for example, by means of thin layer chromatography.

In process step b2, a procedure is best used in which the compound of the formula IVa is reacted with an oxidant such as pyridinium chlorochromate, pyridinium dichromate, tetrapropylammonium ruthenate or DMSO in the presence of acetic anhydride, oxalyl chloride or trifluoroacetic anhydride in equimolar amounts or in an excess of up to 50-fold, if desired in an inert solvent such as chloroform, carbon tetrachloride, methylene chloride or hexane, until the reaction is complete.

The reaction temperatures in this case are between −70° C. and +100° C., when using a solvent preferably between the solidification point and the boiling point of the solvent, in particular between −70° C. and +40° C. The reaction times are 1 to 180 hours, preferably 1 to 48 hours, particularly preferably 1 to 28 hours. Completion of the reaction can be determined, for example, by means of thin layer chromatography (TLC).

The oxidants for process step b2 are commercially available.

In process step b3, a procedure is best used in which the compound of the formula V from process step b2 is stereo-selectively reduced using an alkali metal or alkaline earth metal borohydride, for example using $NaBH_4$ in a solvent, preferably in an alcohol, such as methanol, ethanol or isopropanol, or in an ether such as tetrahydrofuran. Particularly preferred reductants are alkyl borohydrides, for example ®LS-Selectride (Aldrich, Steinheim, FRG).

The reaction temperatures in this case are between −70° C. and +100° C., preferably between the solidification point and the boiling point of the solvent, in particular between −70° C. and +10° C. The reaction times are 1 to 60 hours, preferably 5 to 20 hours. Completion of the reaction can be determined, for example, by means of TLC checking.

In process step b4, a procedure is best used in which the compound of the formula IVc is reacted in the presence of catalytic amounts of a Lewis acid, in equimolar amounts or in an excess of up to 50-fold of an alcohol-water mixture, in particular an isopropanol-water mixture, if appropriate in an inert solvent such as chloroform, methylene chloride, THF, ethyl acetate or dioxane, until the reaction is complete. Suitable Lewis acids are, for example, copper, iron or lithium halides, in particular $CuCl_2$, $FeCl_3$ or LiBr.

The concentration of the Lewis acid, relative to the compound of the formula IVc, is 0.1 to 5% by weight, preferably 0.1 to 1% by weight. The reaction temperatures in this case are between −40° C. and +100° C., in particular between 0° C. and 30° C., when using a solvent preferably between the solidification point and the boiling point of the solvent, in particular between 0° C. and 30° C. The reaction times are 1 to 180 minutes, preferably 5 to 60 minutes Completion of the reaction can be determined, for example, by means of thin layer chromatography.

In process step b5, a procedure analogous to that in process step a1 is best used. The compound of the formula IIb is disastereoselectively reduced to a compound of the formula IIIc using an alkoxydialkylborane and $NaBH_4$ or disastereoselectively reduced to a compound of the formula IIId using $NaHB(OAc)_3$ or $NH_4HB(OAc)_3$.

In process step b6, a procedure analogous to that in process step a2 is best used. The compound of the formula IIIc or IIId is oxidized regioselectively to the δ-lactone of the formula Ic or Id in the presence of a ruthenium complex.

In process step b7, a procedure analogous to that in process step a3 is best used. The compounds Ic or Id having a straight-chain or branched alkenyl radical are reacted with hydrogen as described in process step a3 to give the corresponding compounds of the formula Ic or Id having a straight-chain or branched alkyl radical.

In process step c1), a procedure is best used in which, starting from the compounds Ia, Ib, Ic or Id in which $R^1$ is straight-chain or branched alkyl or alkenyl having 3 to 15 carbon atoms, the compound is transesterified with an alcohol in the presence of sodium hydride to give the corresponding compound Va, Vb, Vc or Vd.

The reaction temperatures in this case are between the solidification point and the boiling point of the solvent, in particular between −20° C. and +30° C. The reaction times are between 3 and 10 hours. Completion of the reaction can be determined, for example, using thin layer chromatography (TLC).

In process step c2), a procedure is best used in which the Compounds Va, Vb, Vc or Vd from process step 1 are ketalyzed with acetone or dimethoxypropane in the presence of zinc chloride to give the Compounds VIa, VIb, VIc or VId.

The reaction temperatures in this case are between 20° C. and 70° C. The reaction times are 5 to 60 hours, preferably 8 to 20 hours.

In process step c3), the alkyl side chain R of the compounds VIa, VIb, VIc and VId is shortened to the methylhydroxy group by ozonolysis and addition of sodium borohydride.

Ozonolysis is carried out by known methods (Organikum, 14th Edition, 1975, page 295, VEB-Verlag).

The compounds of the formula Ia, Ib, Ic or Id, in which $R^1$ is a methylhydroxy group, are obtained from the corresponding compounds VIIa, VIIb, VIIc and VIId by acid cleavage of the protecting groups. This is carried out, for example, using trifluoroacetic acid in an inert solvent.

Chain-lengthening of the alkyl side chain $R^1$ is carried out, starting from the compound of the formula IIa, by processes known from the literature. Chain-lengthening is carried out, for example, by ozonolysis to the aldehyde and subsequent carbonyl olefination, for example according to Wittig (Organikum, VEB-Verlag, 1975, pages 295 and 434).

The purification, isolation and working-up of the substances is carried out by customary methods; for example the reaction products can be purified by chromatography on polar support materials such as silica gel or ®Sephadex LH 20 using solvents such as lower alkanols such as methanol, chloroform, dichloromethane or ethyl acetate, or methanol/chloroform mixtures or ethyl acetate/hexane mixtures but also by extractive methods such as liquid/liquid extraction or solid/liquid extraction.

The compounds of the formula I and their physiologically tolerable salts are very highly suitable, owing to their useful pharmacological properties, for use as medicaments.

The invention therefore also relates to pharmaceuticals containing at least one compound of the formula Ia, Ib, Ic or Id. The pharmaceuticals are preferably suitable for the prophylaxis and/or therapy of disorders of the metabolism due to cholesterol and cholesterol-like substances.

The pharmaceuticals according to the invention are in general administered orally or parenterally, but rectal administration is also possible in principle. Suitable solid or liquid pharmaceutical preparation forms are, for example, granules, powders, tablets, coated tablets, (micro)capsules, suppositories, syrups, emulsions, suspensions, aerosols, drops or injectable solutions in ampoule form and also preparations with protracted release of active compound, during whose preparation excipients and additives and/or auxiliaries such as disintegrants, binders, coating agents, swelling agents, glidants or lubricants, flavorings, sweeteners or solubilizers are customarily used. Frequently used excipients or auxiliaries which may be mentioned are, for example, magnesium carbonate, titanium dioxide, lactose, mannitol and other sugars, talc, lactoprotein, gelatin, starch, vitamins, cellulose and its derivatives, animal and vegetable oils, polyethylene glycols and solvents, such as, for example, sterile water, alcohol, glycerol and polyhydric alcohols.

The pharmaceutical preparations are preferably prepared and administered in dosage units, each unit containing a specific dose of at least one compound of the formula Ia, Ib, Ic or Id as the active constituent. In the case of solid dosage units such as tablets, capsules and suppositories, this dose can be up to about 500 mg, but preferably about 50 to 300 mg, and in the case of injection solutions in ampoule form up to about 150 mg, but preferably about 10 to 100 mg.

For the treatment of an adult patient, depending on the activity of the compounds according to formula Ia, Ib, Ic or Id in humans, daily doses of about 20 to 500 mg of active compound, preferably about 50 to 300 mg, are indicated for oral administration and of about 5 to 300 mg, preferably about 10 to 100 mg, for intravenous administration. Under certain circumstances, however, higher or lower daily doses may also be appropriate. The administration of the daily dose can be carried out either by single administration in the form of an individual dosage unit or else several smaller dosage units or by multiple administration of subdivided doses at specific intervals.

The pharmaceuticals according to the invention are prepared by bringing at least one compound of the formula Ia, Ib, Ic or Id into the or a suitable administration form using customary excipients and, if desired, additives and/or auxiliaries.

The compound of the formula Ia has outstanding activity as an inhibitor of cholesterol biosynthesis. It can therefore be employed as a hypolipidemic agent. Owing to its pharmacological properties, the compound of the formula Ia is suitable for the treatment and prophylaxis of disorders of the metabolism due to cholesterol and cholesterol-like substances.

The compounds of the formulae Ia, Ib, Ic and Id are furthermore suitable as flavorings and fragrances.

The invention is illustrated in greater detail below with examples.

All compounds obtained according to the following examples were characterized by means of $^1$H-NMR and/or $^{13}$C-NMR and/or IR and/or C,H analysis and/or mass spectrum.

Preparation of the Compound of the Formula IIa a) Preparation of a spore suspension of the product strain DSM 4356: 100 ml of nutrient solution (4 g of yeast extract, 10 g of malt extract, 4 g of glucose, 1 l of tap water, pH before sterilization 7.3) in a 500 ml Erlenmeyer flask are inoculated with the strain and incubated for 72 hours at 27° C. and 120 rpm on a rotating shaker 20 ml of culture fluid are then uniformly distributed and decanted into a 500 ml Erlenmeyer flask containing the nutrient medium of the abovementioned composition, to which 20 g of agar/l have been added for solidification. The cultures are incubated at 27° C. for 10 to 14 days. The spores from one flask formed after this time are suspended using 500 ml of deionized water, which contains one drop of a commercial nonionic surfactant, and immediately reused or stored at −22° C.

b) Preparation of a culture or preculture of a product strain in the Erlenmeyer flask:

A 500 ml Erlenmeyer flask containing 100 ml of a nutrient solution of composition 2% meat meal, 10% malt extract, 1% calcium carbonate and water to 100% (pH 7.2 before autoclaving) is inoculated with a culture raised in a slant tube or with 0.2 ml of spore suspension and incubated on a shaker at 120 rpm and 27° C. The maximum production of the desired substance is achieved after 72 hours 10 and 100 l fermenters are inoculated to 5% strength with a 48 hours old submerse culture of the same nutrient solution.

c) Preparation of the compound of the formula IIa:

A 10 l fermenter is operated under the following conditions:

| Nutrient medium: | 2% mannitol |
| | 2% soya flour |
| | pH 7.2 |
| Incubation time: | 72 hours |
| Incubation temperature: | 30° C. |
| Stirrer speed: | 250 rpm |
| Aeration: | 4 l of air/min. |

The development of foam can be suppressed by repeated addition of a few drops of ethanolic polyol solution. The production maximum is achieved after about 70 hours (pH TM 5.3). The yields are about 20 mg/l.

d) Isolation of the compound of the formula II

After fermentation of the product strains, the culture broth is filtered with the addition of 2% Celite as a filter aid. The mycelium is extracted with ethyl acetate and the organic phase is evaporated. The culture filtrate is dried and the residue is extracted with ethyl acetate. The crude product is chromatographed on a silica gel column (silica gel 60, Macherey-Nagel) using ethyl acetate/hexane (1:2, v:v).

EXAMPLE 1

(+)-(3S,5R,8E)-1,3,5-Trihydroxy—8-decene (compound 3a)

1 g (5.4 mmol) of the compound of the formula IIa, in which $R^1$ is 2-pentene, is stirred at room temperature in 50 ml of tetrahydrofuran for 15 min with 8.6 ml of a 1 molar triethylborane solution in tetrahydrofuran (8.6 mmol). After cooling to −70° C., 4.3 ml of methanol and 0.4 g (10.7 mmol) of sodium borohydride are added and the reaction mixture is stirred at this temperature for a further 3 h. For working-up, 30 ml of a saturated sodium hydrogen carbonate solution are added to this mixture and it is extracted three times using 100 ml of ethyl acetate in each case. The ester phase is dried over sodium sulfate. After filtering off, the solvent is removed by distillation in vacuo and an oily product is obtained. This is additionally treated with methanol five times and distilled in vacuo so that excess borane is removed. The residue which remains is purified on silica gel using acetone:hexane (2:3) and gives the compound 3a in a yield of 0.82 g (81%) as a colorless oil.

Rf=0.40 ($CH_2Cl_2:CH_3OH/9:1$); $[\alpha]^D_{20}+4.4°$ (c=1, $CH_2Cl_2$).

Analysis for $C_{10}H_{20}O_3$ (188.27): calculated: C 63.8; H 10.7; found : C 63.9; H 10.7;

$^1$H-NMR (400 MHz) δ=1.5–1.7 (m, H-2, H-4, H-6, H-10); 2.1 (m, 2H, H-7); 3.75 (m, 3H, H-1, H-5); 4.1 (m, 1H, H-3); 5.45 (m, 2H, H-8, H-9).

$^{13}$C-NMR (100 MHz) δ=17.8 (C-10); 28.4 (C-7); 37.7 (C-6); 39.0 (C-2); 43.0 (C-4); 60.4 (C-1); 71.5 (C-5); 72.0 (C-3); 125.35 (C-9); 130.7 (C-8);

IR ($CHCl_3$) m=3200–3600 (OH).

EXAMPLE 2

(+)-(3S,5S,8E)-1,3,5-Trihydroxy-8-decene (compound 3b)

4.3 ml of glacial acetic acid are added dropwise at −70° C. to a suspension of 900 mg (23.8 mmol) of sodium borohydride in 25 ml of tetrahydrofuran during the course of 10 min and the mixture is stirred at this temperature for 2 h. After addition of 1 g (5.4 mmol) of the compound of the formula IIa, in which $R^1$ is 2-pentene, in 5 ml of tetrahydrofuran, a further 20 ml of glacial acetic acid are added dropwise during the course of 30 min and the reaction mixture is stirred at this temperature for a further 2 h.

After complete conversion, checked by TLC, the mixture is treated with 10 ml of water and 30 ml of saturated sodium hydrogen carbonate solution and extracted three times using 100 ml of ethyl acetate each time. The organic phase is washed a further three times with 50 ml of water each time and then dried over sodium sulfate. After removal of the solvent by distillation in vacuo, the residue is purified by chromatography on silica gel using acetone:hexane (2:3) and gives 78% of the compound 3b (0.8 g).

Rf=0.37 ($CH_2Cl_2:CH_3OH/9:1$); $[\alpha]^D_{20}=+9.5°$ (c=1, $CH_2Cl_2$).

Analysis for $C_{10}H_{20}O_3$ (188.27): calculated: C 63.8; H 10.7; found : C 63.7; H 10.5.

$^1$H-NMR (400 MHz) δ=1.65–1.85 (m, 9H, H-2, H-4, H-6, H-10); 2.1 (m, 2H, H-7); 3.9 (m, 3H, H-1); 4.0 (m, 1H, H-5); 4.2 (m, 1H, H-3); 5.45 (m, 2H, H-8, H-9).

$^{13}$C-NMR (100 MHz) δ=17.9 (C−10); 29.0 (C-7); 37.0 (C-6); 38.3 (C-2); 42.6 (C-4); 61.9 (C-1); 69.15 (C-5); 69.8 (C-3); 125.6 (C-9); 130.7 (C-8).

IR ($CHCl_3$) m=3200–3600 (OH).

EXAMPLE 3

(+)-(3R,5R,8E)-3-hydroxy-5-dec-8-enolide (compound 1a)

300 mg (1.59 mmol) of the compound 3a according to Example 1 are dissolved in 15 ml of benzene and treated with 1.39 g (1.59 mmol) of tris(triphenylphosphine)-ruthenium(II) chloride. The mixture is stirred at room temperature for 3 days. After removal of the benzene by distillation in vacuo, the tarry black residue is dissolved in 2 ml of acetone and purified on silica gel using ethyl acetate/hexane (1:1). The compound results as a colorless oil in 68% yield (200 mg).

Rf=0.51 (ethyl acetate:hexane/3 1); $[\alpha]^D_{20}=+54.9°$ (c=0.83, $CH_2Cl_2$).

Analysis for $C_{10}H_{16}O_3$ (184.24): calculated C 65.2; H 8.75; found : C 65.4; H 8.5.

$^1$H-NMR (400 MHz) δ=1.64 (m, 4H, J=5.5 Hz, J01.5 Hz, H-10, H-4,); 1.78 (m, 2H, H-4, H-6); 1.95 (m, 1H, H-6), 2.15 (m, 2H, H-7); 2.61 (d,d, 1H, J=17 Hz, J=2.7 Hz, H-2ax); 2.72 (d,d, J=17 Hz, J=4.7 Hz, H-2eq); 4.36 (m, 1H, H-3eq); 4.7 (m, 1H, H-5ax); 5.4 (m, 1H, H-8); 5.45 (m, 1H, H-9).

$^{13}$C-NMR (100 MHz) δ=17.8 (C-10); 27.8 (C-7); 35.4 (C-4); 36.1 (C-6); 38.7 (C-2); 62.7 (C-3); 75.2 (C-5); 126.1 (C-9); 129.75 (C-8); 170.4 (C-1);

IR ($CHCl_3$) m=3200–3600 (OH), 1740 (lactone).

EXAMPLE 4

(−)-(3R,5S,8E)-3-Hydroxy-5-dec-8-enolide (compound 1b)

300 mg (1.59 mmol) of the compound 3b according to Example 2 are prepared under the same conditions as in Example 3.

The lactone (compound 1b) gave 220 mg (75%) as a colorless oil.

Rf=0.49 (ethyl acetate:hexane/3:1); $[\alpha]^D_{20}=-25.17°$(c=0.146, $CH_2Cl_2$).

Analysis for $C_{10}H_{20}O_3$ (184.24): calculated: C 65.2; H 8.75; found : C 65.6; H 8.8.

EXAMPLE 5

(+)-(3R,5R)- 3-Hydroxy—5-decanolide (compound 6a)

200 mg (1.1 mmol) of the compound 1a according to Example 3 are dissolved in 20 ml of ethyl acetate, treated with 30 mg of Pd/active carbon and hydrogenated at atmospheric pressure and room temperature for 8 hours. After filtration, the catalyst is washed with 20 ml of ethyl acetate; the solution is distilled in vacuo and the residue which remains is purified on silica gel using ethyl acetate:hexane (1:1). The colorless oily product (compound 6a) gives 190 mg (94%).

Rf 0.54 (ethyl acetate:hexane/3:1); $[\alpha] = +35.07°$ (c=1.5, $CH_2Cl_2$).

Analysis for $C_{10}H_{18}O_3$ (186.25): calculated: C 64.5; H 9.7; found : C 64.9; H 8.1.

$^1$H-NMR (360 MHz $CDCl_3$) $\delta = 0.9$ (t, 3H, J=6.9 Hz, H-10); 1.2–1.74 (m, 4H, 8H, H-6, H-8, H-9); 1.98 (d,d,d,d, 1H, J=14.4 Hz, J=4.0 Hz, J=2.9 Hz, J=1.7 Hz, H-4eq); 2.65 (d,d,d, 1H, J=17.6 Hz, J=3.7 Hz, J=1.7 Hz, H-2eq); 2.72 (d,d, 1H, J=17.6 Hz, J=5.1 Hz, H-2ax); 4.38 (m, 1H, H-3eq); 4.72 (m, 1H, H-5).

$^{13}$C-NMR (90.55 MHz) $\delta=13.9$ (C-10); 22.5 (C-9); 24.5 (C-7); 31.5 (C-8); 35.5 (C-6); 36.0 (C-4); 38.6 (C-2); 62.8 (C-3); 75.9 (C-5); 170.6 (C-1).

IR ($CHCl_3$) m=3200–3600 (OH), 1740 (lactone).

EXAMPLE 6

(−)-(3R,5S)- 3-Hydroxy-5-decanolide (compound 6b)

200 mg (1.1 mmol) of the compound 1b according to Example 4 are hydrogenated as described in Example 5 and purified.

The lactone (compound 6b) is obtained as a colorless oil with a yield of 185 mg (92%).

Rf=0.53 (ethyl acetate:hexane/3 1); $[\alpha] = -39.25°$ (c=0.91, $CH_2Cl_2$).

Analysis for $C_{10}H_{18}O_3$ (186.25): calculated: C 64.5; H 9.7; found : C 64.5; H 8.5.

$^1$H-NMR (400 MHz) $\delta=0.9$ (t, 3H, J=6.9 Hz, H-10); 1,32 (m, 4H, H-8, H-9); 1.39 (m, 1H, H-7); 1.49 (m, 1H, H-7); 1.57 (m, 1H, H-4eq); 1.63 (m, 1H, H-6); 1.73 (m, 1H, H-6); 2.25 (d,d,d,d, 1H, J=13.7 Hz, J=5.5 Hz, J=3.0 Hz, J=1.4 Hz, H-4eq); 2.45 (d,d, 1H, J=17.1Hz, J=7.9 Hz, H-2ax); 2.89 (d,d,d, 1H, J=17.1 Hz, J=5.9 Hz, J=1.4 Hz, H-2eq); 4.2 (m, 2H, H-3, H-5).

$^{13}$C-NMR (99.55 MHz, $CDCl_3$) $\delta=13.9$ (C-10); 22.5 (C-9); 24.5 (C-7); 31.5 (C-8); 35.6 (C-6); 37.9 (C-4); 39.5 (C-2); 63.9 (C-3); 77.3 (C-5); 170.7 (C-1).

EXAMPLE 7

(+)-(2R,4S)-
4-Hydroxy-2-methoxy-2-(3E-pentenyl)-tetrahydropyran (compound 4a)

(−)-(2S,4S)-
4-Hydroxy-2-methoxy-2-(3E-pentenyl)-tetrahydropyran (compound 4b)

20 g (54 mmol) of the compound of the formula IIa, in which $R^1$ is 2-pentene, are stirred at room temperature in 500 ml of methanol with 600 mg of $FeCl_3$ for 15 min. The reaction mixture is then adjusted to pH 7 with sodium hydrogen carbonate solution and concentrated. Chromatographic separation on silica gel using ethyl acetate/hexane/triethylamine (1:4:0.5) gives 65% of compound 4a (7 g) and 5% of compound 4b (0.538 g).

Compound 4a: Rf=0.36 (ethyl acetate/hexane 1:2); $[\alpha]^{D}_{20}= +82.6°$ (c=2.8, $CH_2Cl_2$).

Analysis for $C_{11}H_{20}O_3$ (200.28): calculated: C 66.0; H 10.1; found : C 65.8; H 10.4.

Compound 4b: Rf=0.60 (ethyl acetate/hexane 1:2); $[\alpha]^{D}_{20}= -66.0°$ (c=3.0, $CH_2Cl_2$).

Analysis for $C_{11}H_{20}O_3$ (200.28): calculated: C 66.0; H 10.1; found : C 66.0; H 10.7.

EXAMPLE 8

(+)-(2S)- 2-Methoxy-2-(3E-pentenyl)-4-tetrahydropyran (compound 5)

7 g (32.7 mmol) of the compound 4a from Example 7 are stirred with 800 mg (2.3 mmol) of tetrapropylammonium ruthenate (TPAP) and 8 g (68.3 mmol) of N-methyl-morpholine-N-oxide in 200 ml of $CH_2Cl_2$ for 8 h. The reaction mixture is diluted with 300 ml of $CH_2Cl_2$ and washed twice with 400 ml of a 10% strength sodium hydrogen sulfite solution and five times with water. The organic phase is dried over sodium sulfate, filtered through Celite and concentrated. Compound 5 is obtained with a yield of 5.8 g (89.6%).

Rf=0.73 (ethyl acetate:hexane/3:1); $[\alpha]^{D}_{20}= +75.9$ (c=1.3, $CH_2Cl_2$).

Analysis for $C_{11}H_{18}O_3$ (198.26): calculated: C 66.65; H 9.15; found : C 66.8; H 9.4.

EXAMPLE 9

(+)-(2S,4R)-4-hydroxy-2-methoxy-2-(3E-pentenyl)-(tetrahydropyran (compound 4c)

5.8 g (29.3 mmol) of compound 5 from Example 8 are dissolved at −70° C. in 350 ml of isopropanol, 2.2 g (5.2 mmol) of sodium borohydride are added and the mixture is stirred at this temperature for 5 h To eliminate the excess $NaBH_4$, 10 ml of acetone dried over alumina are added and the mixture is stirred at room temperature for 15 min. The mixture is freed from solvent by distillation in vacuo; the residue which remains is purified on silica gel using ethyl acetate/hexane/triethylamine (1:4:0.5) and gives 4.8 g (82%) of compound 4c and 0.54 g (9.2%) of compound 4a (see Example 7). If LS-Selectride is used instead of NaBH , only 4c is formed.

Compound 4c: Rf=0.60 (ethyl acetate/hexane 1:2) $[\alpha]^{D}_{20}=64.5°$ (c=1.5, $CH_2Cl_2$).

Analysis for $C_{11}H_{20}O_3$ (200.28): calculated: C 66.0; H 10.1; found : C 66.0; H 10.2.

EXAMPLE 10

(−)-(3R,8E)- 1,3-Dihydroxy-8-decen-5-one (compound 2b)

4.6 g (23.0 mmol) of compound 4c from Example 9 are dissolved with 45 mg of $FeCl_3$ in 45 ml of isopropanol and 45 ml of water and the mixture is stirred at room temperature for 30 min. The pH of the reaction mixture is adjusted to pH 7 to 8 using sodium hydrogen carbonate solution and the mixture is concentrated to a syrup on a rotary evaporator. The residue which remains is dissolved in 30 ml of $CH_2Cl_2$ and filtered; yield 3.9 g (92%) of compound 2b. Rf=0.48 (ethyl acetate/hexane/methanol 2:1:0.1; $[\alpha]^{D}_{20}= -23°$ ((c=1, $CH_2Cl_2$).

Analysis for $C_{10}H_{18}O_3$ (186.25): calculated C 64.5; H 9.75; found : C 64.2; H 10.0.

¹H-NMR (300 MHz) δ=1.6 (m, 4H, H-2, H-10); 2.25 (m, 1H, H-7); 2.5 (t, 1H, J=7 Hz, H-6); 2.6 (d, 1H, J=6.5 Hz, H-4); 3.8 (t, 2H, J=5 Hz); 4.3 (m, 1H, H-3); 5.45 (m, 2H, H-8, H-9).

¹³C-NMR (90.55 MHz) δ=17.7 (C-10); 37.9 (C-2); 43.3 (C-6); 49.3 (C-4); 60.7 (C-1); 67.4 (C-3); 126.1(C-9); 129 2 (C-8); 211.2 (C-5).

EXAMPLE 11

(−)-(3R,5S,8E)- 1,3,5-Trihydroxy-8-decene (compound 3c)

1 g (5.4 mmol) of compound 2b from Example 10 is stirred at room temperature in 50 ml of tetrahydrofuran with 8.6 ml of a 1 molar triethylborane solution in tetrahydrofuran (8.6 mmol) for 15 min. After cooling to −70° C., 4.3 ml of methanol and 0.4 g (10.7 mmol) of sodium borohydride are added and the reaction mixture is stirred at this temperature for a further 3 h. For working-up, 30 ml of a saturated sodium hydrogen carbonate solution are added to the mixture and it is extracted three times using 100 ml of ethyl acetate in each case. The ester phase is dried over sodium sulfate After filtering off, the solvent is removed by distillation in vacuo and an oily product is obtained. This is treated with methanol a further five times and distilled in vacuo so that excess borane is removed The residue which remains is purified on silica gel using acetone:hexane (2:3) and gives the compound 3c in a yield of 0.84 g (83%) as a colorless oil.

Rf=0.40 ($CH_2Cl_2:CH_3OH/9:1$); $[\alpha]^D_{20}=-4.2°$ (c=1, $CH_2Cl_2$).

Analysis for $C_{10}H_{20}O_3$ (188.27): calculated: C 63.8; H 10.7; found : C 63.5; H 10.9.

The spectroscopic data are identical to those of compound 3a from Example 1.

EXAMPLE 12

(−)-(3R,5R,8E)-1,3,5-Trihydroxy-8-decene (compound 3d)

4.3 ml of glacial acetic acid are added dropwise at −70° C. to a suspension of 900 mg (23.8 mmol) of sodium borohydride in 25 ml of tetrahydrofuran during the course of 10 min and the mixture is stirred at this temperature for 2 h. After addition of 1 g (5.4 mmol) of compound 2b from Example 10 in 5 ml of tetrahydrofuran, a further 20 ml of glacial acetic acid are added dropwise during the course of 30 min and the reaction mixture is stirred at this temperature for a further 2 h.

After complete conversion determined by TLC, the mixture is treated with 10 ml of water and 30 ml of saturated sodium hydrogen carbonate solution and extracted three times using 100 ml of ethyl acetate each time. The organic phase is washed a further three times using 50 ml of water each time and then dried over sodium sulfate. After removal of the solvent by distillation in vacuo, the residue is purified by chromatography on silica gel using acetone:hexane (2:3) and gives compound 3d with a yield of 76% (0.78 g).

Rf=0.37 ($CH_2Cl_2:CH_3OH/9:1$); $[\alpha]^D_{20}=-9.2°$ (c=1, $CH_2Cl_2$).

Analysis for $C_{10}H_{20}O_3$ (188.27): calculated: C 63.8; H 10.7; found : C 63.4; H 10.3.

The spectroscopic data are identical to those of compound 3b from Example 2.

EXAMPLE 13

(+)-(3S,5S,8E)- 3-Hydroxy-5-dec-8-enolide (compound 1c)

300 mg (1.59 mmol) of compound 3c from Example 11 are dissolved in 15 ml of benzene and treated with 1.39 g (1.59 mmol) of tris(triphenylphosphine)ruthenium(II) chloride. The mixture is stirred at room temperature for 3 days. After removal of the benzene by distillation in vacuo, the tarry black residue is dissolved in 2 ml of acetone and purified on silica gel using ethyl acetate/hexane (1:1).

The lactone (compound 1c) results as a colorless oil in 72% yield (210 mg).

Rf=0.51 (ethyl acetate:hexane/3:1); $[\alpha]^D_{20}=-52.0°$ (c=0.92, $CH_2Cl_2$).

Analysis for $C_{10}H_{16}O_3$ (184.24): calculated C 65.2; H 8.75; found : C 65.6; H 8.3.

The spectroscopic data are identical to those of the compound from Example 3.

EXAMPLE 14

(−)-(3S,5R,8E)- 3-Hydroxy-5-dec-8-enolide (compound 1d)

300 mg (1.59 mmol) of compound 3d from Example 12 are reacted under the same conditions as indicated in Example 13.

The lactone obtained (compound 1d) gave a yield of 210 mg (73%) as a colorless oil.

Rf=0.49 (ethyl acetate:hexane/3:1); $[\alpha]=+25.5°$ (c=0.14, $CH_2Cl_2$).

Analysis for $C_{10}H_{20}O_3$ (184.24): calculated: C 65.2; H 8.75; found : C 65.6; H 8.3.

The spectroscopic data are identical to those of compound 1b from Example 4

EXAMPLE 15

(+)-(3S,5S)- 3-Hydroxy-5-decanolide (compound 6c)

200 mg (1.1 mmol) of compound 1c from Example 13 are dissolved in 20 ml of ethyl acetate, treated with 30 mg of Pd/active carbon and hydrogenated at atmospheric pressure and room temperature for 8 hours. After filtration, the catalyst is washed with 20 ml of ethyl acetate; the solution is distilled in vacuo and the residue which remains is purified on silica gel using ethyl acetate:hexane (1:1). The colorless oily product (compound 6c) gives a yield of 180 mg (92%).

Rf 0.54 (ethyl acetate:hexane/3:1); $[\alpha]^D_{20}=-34.1°$ (c=1.5, $CH_2Cl_2$).

Analysis for $C_{10}H_{18}O_3$ (186.25): calculated: C 64.5; H 9.7; found : C 64.8; H 8.9.

The spectroscopic data are identical to those of compound 6a from Example 5.

EXAMPLE 16

(−)-(3S,5R)- 3-Hydroxy-5-decanolide (compound 6d)

200 mg (1.1 mmol) of compound 1d from Example 14 are hydrogenated as described in Example 15 and purified.

The lactone (compound 6d) is obtained as a colorless oil and gives a yield of 185 mg (92%).

Rf=0.53 (ethyl acetate:hexane/3:1); $[\alpha]^D_{20}=+40.1°$ (c=1.0, $CH_2Cl_2$).

Analysis for $C_{10}H_{18}O_3$ (186.25): calculated: C 64.5; H 9.7; found : C 64.5; H 8.9.

The spectroscopic data are identical to those of compound 6b from Example 6.

EXAMPLE 17

(3S,5S,6E,8E)- 1,3,5-Trihydroxy-6,8-decadiene (compound 3e)

1 g (5.4 mol) of the compound of the formula IIa, in which $R^1$ is 2,4-dipentene, is reacted as indicated in Example 1.

Analysis for $C_{10}H_{18}O_3$ (186.27): calculated: C 64.49; H 9.79; found : C 64.1; H 9.7.

$^1$H-NMR (400 MHz) $\delta = 1.5$–$2.0$ m; 3.9 (m, 2H, H-1); 4.25 (m, 1H, H-3); 4.55 (m, 1H, H-5); 5.6–5.7 (m, 3H); 6.1 (m, 1H); 6.25 (m, 1H).

EXAMPLE 18

(3S,5R,6E,8E)- 3-Hydroxy-5-deca-6,8-dienolide (compound 1e)

300 mg of compound 3e according to Example 17 are reacted as indicated in Example 3.

Analysis for $C_{10}H_{14}O_3$ (182.22): calculated: C 65.92; H 7.74; found C 65.8; H 7.6.

$^{13}$C-NMR (100 MHz) $\delta = 18.0$ (C-1); 36.4 (C-9); 38.7 (C-2); 62.55 (C-3); 76.0 (C-5); 127.0; 130.1; 131.8; 133.0 (C-H); 170.15 (C-1).

EXAMPLE 19

(3R,5S)- 3,6-Dihydroxy-5-hexanolide (compound 1f)

1 g of compound 1e according to Example 18 are dissolved in 30 ml of methanol, treated with 80 mg of sodium hydride and stirred at 25° C. for 5 hours. The mixture is neutralized with 2N HCl, concentrated in a rotary evaporator and dissolved in 30 ml of acetone. The solution is treated with some $ZnCl_2$ and heated to reflux for 12 hours. It is then extracted with a mixture of water and ethyl acetate (1:1, 100 ml each). The ethyl acetate phase is dried over sodium sulfate and, after concentration in a rotary evaporator, the residue is taken up in 150 ml of methanol. Ozonolysis is carried out at −70° C. (Organikum, 14th Edition, 1975, page 295; VEB-Verlag). 1 g of NaBH. is then added and the mixture is stirred for 2 hours. It is then concentrated in a rotary evaporator and extracted with a mixture of water and methylene chloride (1:1; 150 ml each). It is then concentrated in a rotary evaporator and the concentrate is purified on a silica gel column (ethyl acetate/hexane, 1:10 to 10:1). 150 mg of methyl (3R,5S)-3,5-O-isopropylidene-3,5,6-trihydroxyhexanoate are obtained.

Analysis for $C_{10}H_{18}O_5$ (218.25): calculated: C 55.03; H 8.31; found : C 55.1; H 8.2.

Methyl (3R,5S)- 3,5-0-isopropylidene-3,5,6-trihydroxy-hexanoate is converted to (3R,5S)- 3,6-dihydroxy-5-hexanolide at 23° C. over the course of 24 hours using trifluoroacetic acid in 15 equivalents of dichloromethane (U.S. Pat. No. 4,970,313).

EXAMPLE 20

Monolayers of HEP-G2 cells in lipoprotein-free nutrient medium are preincubated for one hour with appropriate concentrations of the substances from Examples 3 and 5 to be tested After addition of the $^{14}$C-labelled biosynthesis precursor [$^{14}$C] sodium acetate, the incubation is continued for 3 hours A part of the cells are then subjected to alkaline hydrolysis, with prior addition of an internal standard of $^3$H-cholesterol. The lipids of the hydrolyzed cells are extracted using a mixture of chloroform/methanol. This lipid mixture is separated by preparative thin layer chromatography after addition of carrier cholesterol, the cholesterol band is isolated after staining and the amount of $^{14}$C-cholesterol formed from the $^{14}$C precursor is determined scintigraphically. Cell protein was determined in an aliquot part of the cells so that the amount of $^{14}$C-cholesterol formed from $^{14}$C precursor in the cell unit per mg of cell protein can be calculated. The control is used to compare the inhibitory action of an added test preparation so that the inhibition of cholesterol biosynthesis can be indicated directly at a specified molar concentration of the test preparation in the medium. In aliquot portions of the cell culture, the integrity of the cell culture and the lack of cell damage is assessed morphologically (light microscopy) by action of the preparation and measured biochemically by determination of lactate dehydrogenase secretion in the incubation medium. Lovostatin was used as a standard preparation. The results are shown in Table 1.

TABLE 1

| Compound | Concentration [M] | Cholesterol in percent of the control |
| --- | --- | --- |
| 1a | $10^{-5}$ | 56 |
| 1a | $10^{-7}$ | 72 |
| 6a | $10^{-5}$ | 45 |
| 6a | $10^{-7}$ | 61 |
| 3e | $10^{-6}$ | 30 |
| 1e | $10^{-6}$ | 30 |

We claim:

1. A process for the preparation of 5-substituted 3R, 5R and 3R, 5S δ-lactones of the formula Ia or Ib

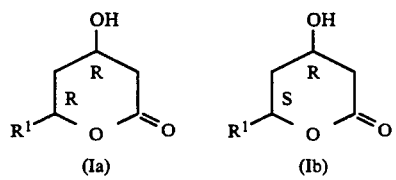

in which $R^1$ is a straight-chain or branched alkyl group having 3 to 15 carbon atoms or a straight-chain or branched alkenyl group having 3 to 15 carbon atoms and 1 to 7 C—C double bonds, which comprises a) disastereoselectively reducing a compound of the formula IIa

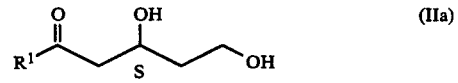

to a compound of the formula IIIa or IIIb

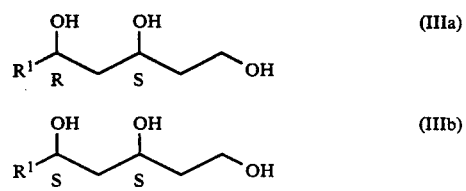

b) regioselectively oxidizing to a compound of the formula Ia or Ib

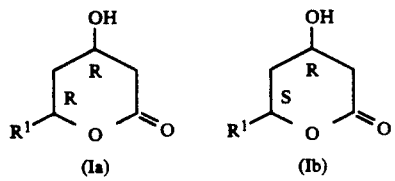

and, optionally, when $R^1$ is a straight-chain or branched alkenyl group, c) hydrogenating the double bonds in the alkylene chain.

2. The process as claimed in claim 1, wherein $R^1$ is a straight chain or branched alkyl group having 3 to 10 carbon atoms or a straight chain or branched alkenyl group having 3 to 10 carbon atoms and 1 to 5 C—C double bonds.

3. The process as claimed in claim 1, wherein $R^1$ is a straight chain or branched alkyl group having 5 carbon atoms or a straight chain or branched alkenyl group having 5 carbon atoms and 1 or 2 C—C double bonds.

4. A process for the preparation of 5-substituted 3S, 5S and 3S, 5R δ-lactones o the formula Ic or Id

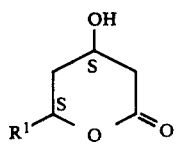

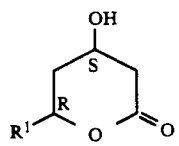

in which $R^1$ is a straight-chain or branched alkyl group having 3 to 15 carbon atoms or a straight-chain or branched alkenyl group having 3 to 15 carbon atoms and 1 to 7 C—C double bonds, which comprises a) acetalating a compound of the formula IIa

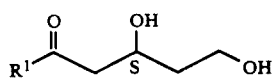

to give a compound of the formula IVa or IVb

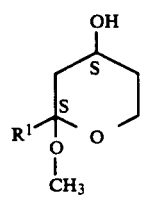

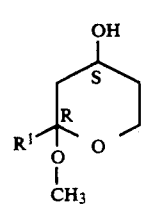

b) oxidizing to give a compound of the formula V

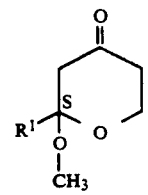

c) disastereoselectively reducing to a compound of the formula IVc

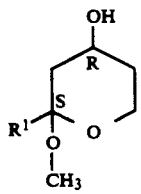

d) deacetalating to to give a compound of the formula IIb

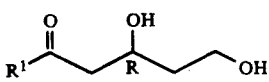

e) diasteroeselectively reducing to a compound of the formula IIIc or IIId

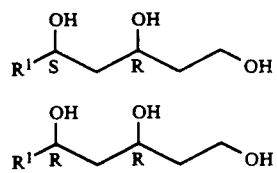

f) regioselectively oxidizing to a compound of the formula Ic or Id

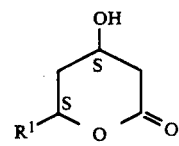

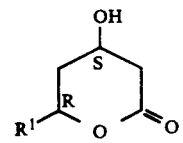

and, optionally, when $R^1$ is a straight-chain or branched alkenyl group, g) hydrogenating the double bonds in he alkylene chain.

5. The process as claimed in claim 4, wherein $R^1$ is a straight chain or branched alkyl group having 3 to 10 carbon atoms or a straight chain or branched alkenyl group having 3 to 10 carbon atoms and 1 to 5 C—C double bonds.

6. The process as claimed in claim 4, wherein $R^1$ is a straight chain or branched alkyl group having 5 carbon atoms or a straight chain or branched alkenyl group having 5 carbon atoms and 1 or 2 C—C double bonds.

7. A process for the preparation of 5-substituted 3R, 5R, 3R, 5S, 3S, 5S and 3S, 5R δ-catones of the formula Ia, Ib, Ic or Id

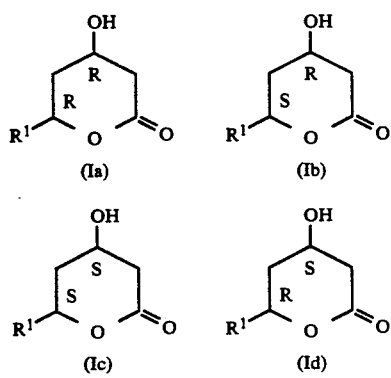

in which $R^1$ is $CH_2OH$, which comprises a) reacting a compound of the formula Ia, Ib, Ic or Id

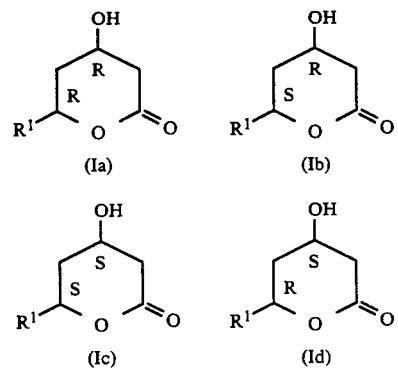

in which $R^1$ is a straight-chain or branched alkyl group having 3 to 15 carbon atoms or a straight-chain or branched alkenyl group having 3 to 15 carbon atoms and 1 to 7 C—C double bonds, with a compound of the formula $R^3$—$O^-$, in which $R^3$ is an alkyl group having 1 to 5 carbon atoms or a tertiary butyl group, to give a compound of the formula Va, Vb, Vc, or Vd

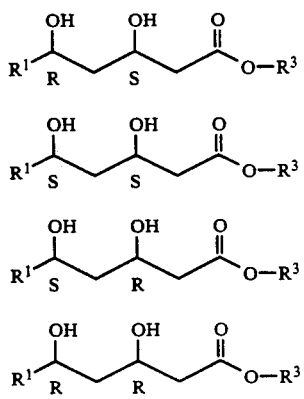

b) ketalizing with acetone or dimethyoxy propane to give a compound of the formula VIa, VIb, VIc or VId

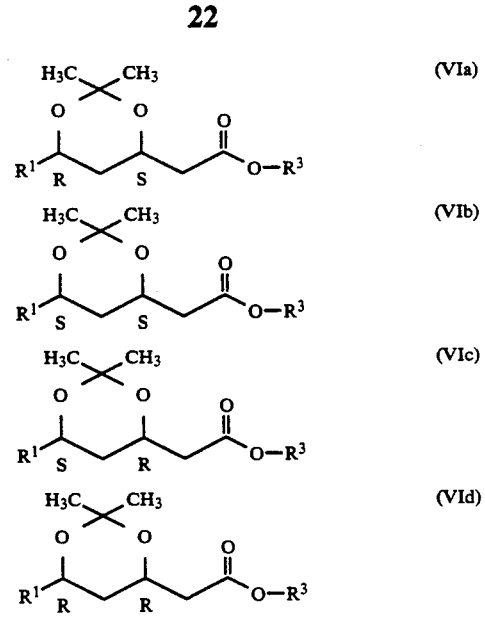

c) oxidizing with ozone to give a compound o the formula VIIa, VIIb, VIIc or VIId

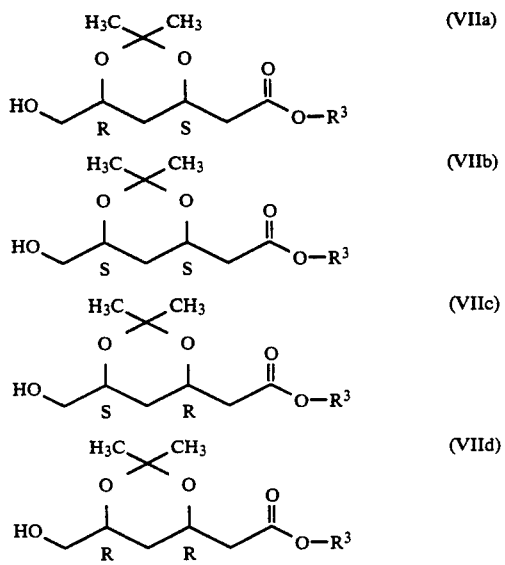

and
d) cleaving with acid to give a compound of the formula Ia, Ib, Ic or Id

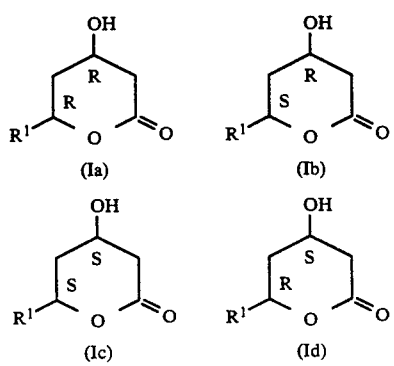

in which $R^1$ is a $CH_2OH$ group.

* * * * *

UNITED STATES PATENT AND TRADEMARK OFFICE
CERTIFICATE OF CORRECTION

PATENT NO. : 5,292,898
DATED : March 08, 1994
INVENTOR(S) : Peter Hammann et al.

It is certified that error appears in the above-indentified patent and that said Letters Patent is hereby corrected as shown below:

Claim 1, column 18, line 49, change "disastereoselectively" to —diastereoselectively—.

Claim 4, column 19, line 25, change "o" to —of—.

Claim 4, column 20, line 11, change "disastereoselectively" to —diastereoselectively—.

Claim 4, column 20, line 30, change "diasteroeselectively" to —diastereoselectively—.

Claim 4, column 20, line 58, change "he" to —the—.

Claim 7, column 21, line 41, change "3to" to —3 to—.

UNITED STATES PATENT AND TRADEMARK OFFICE
CERTIFICATE OF CORRECTION

PATENT NO. : 5,292,898
DATED : March 08, 1994
INVENTOR(S) : Peter Hammann et al.

It is certified that error appears in the above-indentified patent and that said Letters Patent is hereby corrected as shown below:

Claim 7, column 22, line 24, change "o" to --of--.

Signed and Sealed this

Sixth Day of December, 1994

Attest:

BRUCE LEHMAN

*Attesting Officer*　　　　　*Commissioner of Patents and Trademarks*